United States Patent
Kerssens et al.

(10) Patent No.: US 12,243,632 B2
(45) Date of Patent: *Mar. 4, 2025

(54) SYSTEMS AND METHODS FOR PROVIDING CUSTOMIZED THERAPEUTIC PRESENTATIONS

(71) Applicant: SimpleC, LLC, Atlanta, GA (US)

(72) Inventors: Chantal Kerssens, Atlanta, GA (US); Douglas Valmore Nelson, Jr., Atlanta, GA (US)

(73) Assignee: SimpleC, LLC, Marietta, GA (US)

( * ) Notice: Subject to any disclaimer, the term of this patent is extended or adjusted under 35 U.S.C. 154(b) by 49 days.

This patent is subject to a terminal disclaimer.

(21) Appl. No.: 17/985,219

(22) Filed: Nov. 11, 2022

(65) Prior Publication Data

US 2023/0060501 A1    Mar. 2, 2023

Related U.S. Application Data

(63) Continuation of application No. 16/282,556, filed on Feb. 22, 2019, now Pat. No. 11,501,870, which is a continuation of application No. 14/552,591, filed on Nov. 25, 2014, now Pat. No. 10,229,247.

(60) Provisional application No. 61/908,211, filed on Nov. 25, 2013.

(51) Int. Cl.
G06F 9/451 (2018.01)
G16H 10/20 (2018.01)
G16H 10/60 (2018.01)
G16H 20/30 (2018.01)
G16H 20/70 (2018.01)

(52) U.S. Cl.
CPC ............. *G16H 20/70* (2018.01); *G16H 10/20* (2018.01); *G16H 10/60* (2018.01); *G16H 20/30* (2018.01)

(58) Field of Classification Search
CPC ........ G16H 20/70; G16H 10/20; G16H 10/60; G16H 20/30
See application file for complete search history.

(56) References Cited

U.S. PATENT DOCUMENTS

| | | | |
|---|---|---|---|
| 9,251,713 B1 | 2/2016 | Giovanniello et al. | |
| 2011/0119075 A1* | 5/2011 | Dhoble | G16H 10/60 705/2 |
| 2011/0145747 A1 | 6/2011 | Wong et al. | |
| 2011/0245633 A1 | 10/2011 | Goldberg et al. | |

(Continued)

*Primary Examiner* — Maroun P Kanaan
(74) *Attorney, Agent, or Firm* — The Webb Law Firm

(57) ABSTRACT

Systems and methods are provided for providing a personalized therapeutic presentation. A system includes a treatment presentation data store configured to store one or more data structures associated with a personalized therapeutic presentation for a client, where the one or more data structures include client biographic data, client symptom data, client goal data, and media data. A treatment generation engine is configured to generate a treatment presentation for the client based on data stored in the treatment presentation data store, wherein the treatment presentation is designed to treat a symptom identified by the client symptom data to achieve a goal identified by the client goal data, where the treatment presentation comprises a sequential presentation of media identified by the media data that is selected to treat the symptom to achieve the goal.

26 Claims, 13 Drawing Sheets

(56) References Cited

U.S. PATENT DOCUMENTS

| | | | | |
|---|---|---|---|---|
| 2014/0156308 A1* | 6/2014 | Ohnemus | ............... | G16H 40/67 |
| | | | | 705/3 |
| 2014/0324469 A1* | 10/2014 | Reiner | ................... | G16H 50/70 |
| | | | | 705/3 |
| 2014/0372137 A1* | 12/2014 | Tryon | .................... | G16H 10/60 |
| | | | | 705/2 |
| 2015/0033266 A1* | 1/2015 | Klappert | ............ | H04N 21/4314 |
| | | | | 725/52 |
| 2019/0286462 A1 | 9/2019 | Bodnick et al. | | |

\* cited by examiner

Goal Form

| Care Specialist: Full Name | Case ID: 4039X##-0 | Date: dd/mm/yyyy | TO |

I. Checking SYMPTOMS or CONCERNS

Check all that apply

Behavior:
- ☐ 1 delusions
- ☐ 2 hallucinations
- ☐ 3 sad or down (depression)
- ☐ 4 anxiety
- ☐ 5 euphoria/elation
- ☐ 6 apathy/indifference/ uninterested
- ☐ 7 late day confusion ('sundowning')
- ☐ 8 general confusion
- ☐ 9 confused about place (where am I)
- ☐ 10 confused about time (day of the week...)
- ☐ 11 repetitive motor behaviors
- ☐ 12 repetitive vocalizations
- ☐ 13 hypersexuality
- ☐ 14 exit-seeking
- ☐ 15 wandering
- ☐ 16 restless
- ☐ 17 demanding
- ☐ 18 physical aggression
- ☐ 19 verbal aggression
- ☐ 20 agitated/resistive/ uncooperative
- ☐ 21 communication, difficulty
- ☐ 22 communication, unwilling

Sleep:
- ☐ 23 trouble initiating
- ☐ 24 wakes up more than once
- ☐ 25 wakes up (too) early
- ☐ 26 night-time wandering
- ☐ 27 frequent daytime naps

Participation:
- ☐ 28 reluctant to leave the room/house
- ☐ 29 reluctant to socialize or join in
- ☐ 30 confused about how to prepare for or get to an activity Lacks Participation in:
- ☐ 31 physical activities
- ☐ 32 cognitive activities
- ☐ 33 recreation
- ☐ 34 group activities (8 or more)
- ☐ 35 small group activities (2-7 people)
- ☐ 36 1:1 activities
- ☐ 37 solitary activities

Daily Living:
- ☐ 38 bathing
- ☐ 39 dressing
- ☐ 40 toileting
- ☐ 41 transfer
- ☐ 42 oral care
- ☐ 43 grooming
- ☐ 44 change clothes
- ☐ 45 housekeeping
- ☐ 46 medication (take meds)
- ☐ 47 attend breakfast
- ☐ 48 attend lunch
- ☐ 49 attend dinner
- ☐ 50 eating (consume food)
- ☐ 51 hydration (drink water)

Fig. 3

| Goal Form | | Care Specialist: Full Name | Case ID: 4039X##-0 | Date: dd/mm/yyyy | T0 |
|---|---|---|---|---|---|
| Reported Symptoms or Concerns | Description (based on feedback during screen and baseline assessments) | | CG agree? | | CG priority |
| #.Symptom | • <br> Feedback: | | ☐Y ☐N | | |
| #.Symptom | • <br> Feedback: | | ☐Y ☐N | | |
| #.Symptom | • <br> Feedback: | | ☐Y ☐N | | |
| #.Symptom | • <br> Feedback: | | ☐Y ☐N | | |
| #.Symptom | • <br> Feedback: | | ☐Y ☐N | | |
| #.Symptom (new today) | • | | n/a | | |
| #.Symptom (new today) | • | | n/a | | |

*Fig. 4*

| Goal Form | | Care Specialist: Full Name | Case ID: 4039X##-0 | Date: dd/mm/yyyy | T0 |
|---|---|---|---|---|---|
| II. SETTING GOALS: What is the focus and goal of interventions? | | | | | |
| 1. Select most pressing symptoms or concerns. | 2. Quantify current & expected state. | | 3. Define better-than and worse-than-expected outcomes. | | |

| | | Goal 1: | Goal 2: | Goal 3: | Goal 4: |
|---|---|---|---|---|---|
| step 1 ⇨ | capture:<br>• <u>focus</u> (symptom or concern)<br>• <u>goal</u> (expected state) | •<br>• | •<br>• | •<br>• | •<br>• |
| step 2 ⇨ | Current Status<br>• unit of <u>measurement</u> / unit of <u>time</u> | •<br>• | •<br>• | •<br>• | •<br>• |
| 3 | Much Less Than Expected | •<br>• | •<br>• | •<br>• | •<br>• |
| 3 | Somewhat Less Than Expected | •<br>• | •<br>• | •<br>• | •<br>• |
| step 2 ⇨ | Expected<br>• unit of <u>measurement</u> / unit of <u>time</u> | •<br>• | •<br>• | •<br>• | •<br>• |
| 3 | Somewhat More Than Expected | •<br>• | •<br>• | •<br>• | •<br>• |
| 3 | Much More Than Expected | •<br>• | •<br>• | •<br>• | •<br>• |

*Fig. 5*

| Goal Form | Care Specialist: Full Name | Case ID: 4039X##-0 | Date: dd/mm/yyyy | TO |

III. SETTING APPROACH: How do interventions support the goal?

Collect specific ideas, suggestions & requests

GOAL 1:
- Topics:
- Pictures:
- Music:
- Trusted voice:
- Captions:
- Schedules:

GOAL 2:
- Topics:
- Pictures:
- Music:
- Trusted voice:
- Captions:
- Schedules:

GOAL 3:
- Topics:
- Pictures:
- Music:
- Trusted voice:
- Captions:
- Schedules:

GOAL 4:
- Topics:
- Pictures:
- Music:
- Trusted voice:
- Captions:
- Schedules:

*Fig. 6*

SYSTEMS AND METHODS FOR PROVIDING CUSTOMIZED THERAPEUTIC PRESENTATIONS

CROSS REFERENCE TO RELATED APPLICATIONS

This application is a continuation application of U.S. patent application Ser. No. 16/282,556, filed Feb. 22, 2019, which is a continuation application of U.S. patent application Ser. No. 14/552,591, filed Nov. 25, 2014, which claims priority to U.S. Provisional Patent Application No. 61/908,211, filed Nov. 25, 2013, entitled "Systems and Methods for Providing Customized Therapeutic Presentations," all of which are incorporated herein by reference in their entireties.

FIELD

This disclosure is related generally to medical treatment and more particularly to providing customized audio/visual presentations ('therapies') to patients to achieve a care goal.

BACKGROUND

Many people are able to operate functionally throughout a day, performing tasks with little angst or need for reminders. However, aging and the onset of disease can diminish one's capacity to consistently perform day to day tasks in order to feel and be well.

SUMMARY

Systems and methods are included for providing a personalized therapeutic presentation. A system includes a treatment presentation data store configured to store one or more data structures associated with a personalized therapeutic presentation for a client, where the one or more data structures include client biographic data, client symptom data, client goal data, and media data. A treatment generation engine is configured to generate a treatment presentation for the client based on data stored in the treatment presentation data store, wherein the treatment presentation is designed to treat a symptom identified by the client symptom data to achieve a goal identified by the client goal data, where the treatment presentation comprises a sequential presentation of media identified by the media data that is selected to treat the symptom to achieve the goal.

As another example, a computer-implemented method of providing a personalized therapeutic presentation includes receiving an identification of a symptom of a client (e.g., a patient) to be treated and receiving a goal associated with the symptom to be treated. A treatment presentation is automatically designed based on the symptom, the goal, and the recommended therapy approach, where the treatment presentation comprises a sequential presentation of media identified by the treatment presentation. Media identified by the treatment presentation is accessed based on the treatment presentation and an identity of the patient, and the accessed media is presented to the patient.

BRIEF DESCRIPTION OF THE DRAWINGS

FIG. 3 depicts an example symptom survey that is provided to an informant via an informant GUI.

FIG. 4 depicts an example goal form that is provided to a caregiver via a caregiver GUI.

FIG. 5 depicts an example goal definition form that is provided to a caregiver or other technician via a caregiver GUI.

FIG. 6 is a presentation asset identification form utilized in the design of a personalized therapeutic presentation.

DETAILED DESCRIPTION

Figure 1:
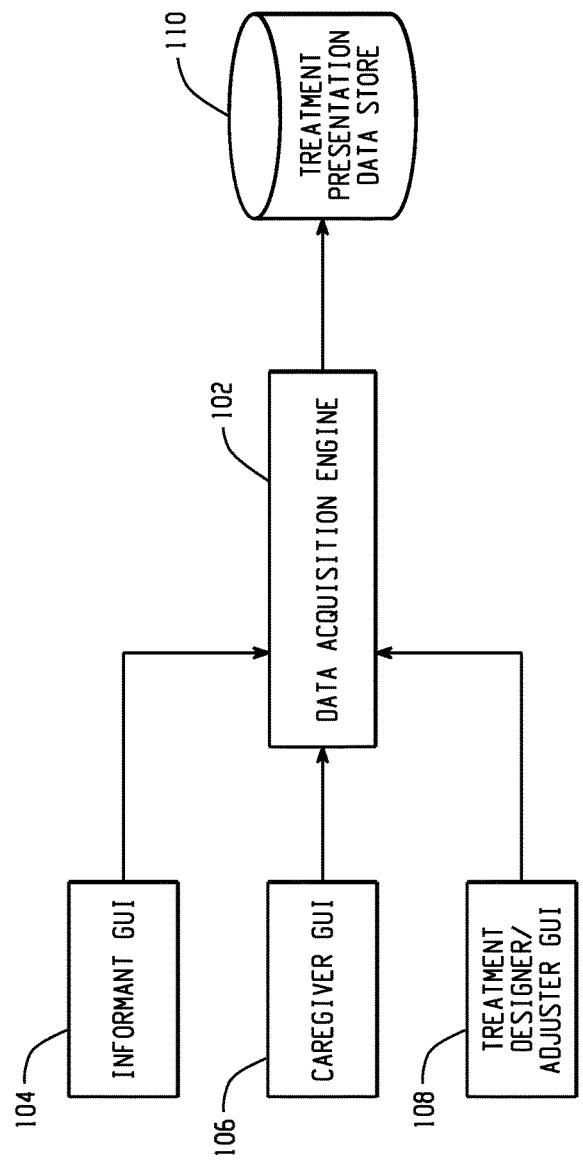
FIG. 1 is a block diagram depicting a computer-implemented system for providing a personalized therapeutic presentation.

FIG. 1 is a block diagram depicting a computer-implemented system for providing a personalized therapeutic presentation. Where a client may struggle with performing certain day to day tasks, such as brushing their teeth, drinking enough water, attending or preparing meals, going to bed, or being on time for an appointment or event (e.g., a doctor's appointment), a system of reminders can be an effective tool for prompting action. Clients may also be prone to stress or anxiety due to age, disease or injury. In such cases, soothing music, pictures, video, or an audio or video recording playback from a familiar person can help alleviate the anxiety and improve wellbeing and function. Further, such anxiety reducing tools can be combined with a system of reminders to reduce stress caused by upcoming tasks to be performed.

The system of FIG. 1 provides a mechanism for designing and delivering personalized therapeutic presentations for a client that can reduce stress of daily life and prompt clients to perform tasks that they should complete for healthy living. A system includes a data acquisition engine 102 that is responsive to a plurality of graphical user interfaces 104, 106, 108. An informant GUI 104 is configured to receive data associated with a symptom of a client. The informant GUI 104 may be accessed by a person trusted by the client (e.g., spouse, family member, friend), a caregiver of the client (e.g., a professional caregiver, such as a doctor, nurse, social worker), the client himself, or other person having interaction with the client. The informant GUI 104 receives an identification of a symptom of the client for which treatment is desired. Treatable symptoms can be wide ranging. Symptoms can include forgetting appointments such as doctor's visits, dentist appointments, church services, and meal times. Symptoms can also include failure to perform daily hygienic and other health activities, such as brushing one's teeth, showering, drinking sufficient water, or going to bed at a proper time. Symptoms can also include general mood deviations, such as anxiety, depression, and anger.

Because symptoms may be many and wide-ranging, informant GUI 104 is configured to receive data on which symptoms are most distressing, upsetting, or difficult to handle. Such symptoms may receive a higher priority ranking and become the object (goal) of intervention. In another example, the informant may simply choose the symptoms or needs they want to focus on depending on their perceived need for support.

In addition to identifying symptoms to be treated, an informant GUI 104 can also be configured to receive identification of goals related to entered symptoms. For example, for a symptom related to attending appointments, a goal may be identified as attending not missing any appointments or not being more than XX minutes late for any appointments. For a symptom of not drinking sufficient water, a goal could be identified as increasing daily water consumption from 2 glasses per day to 5 glasses per day. For a symptom of having high anxiety, a goal may be set for limiting high anxiety episodes to no more than 3 episodes per week.

In addition to identifying symptoms and goals, informant GUI 104 is configured to receive data on the recommended and possible therapy approaches. While some goals are straightforward (e.g., increase hydration), other goals can be achieved in more than one way using more than one therapy. In such cases, informants choose from several common treatment options that align with specific therapies. For instance, for a symptom of high anxiety, one person may choose to play personal photos. Another person may choose a specific calming therapy. A third person may choose to redirect (distract) the client by playing a video of favorite television or radio shows.

The data acquisition engine 102 receives data from the informant GUI 104 and uses that received data to populate records of a treatment presentation data store 110. Data in the treatment presentation data store 110 can be used to generate personalized therapeutic presentations for a client. A presentation may be provided to a client via a number of mediums such as via a tablet computer, a desktop computer, a laptop computer, a mobile phone, a smart phone, or a television. A presentation may take a variety of forms. For example, a presentation may be similar to a slide show presentation, where portions of content are sequentially provided to the client. A portion of content can take the form of audio, video, text, pictures, and other media, where certain of that media is designed to promote a designated goal for the client. Presentations may be continuously played for a client throughout the day, or the presentations may be scheduled to be played at particular times during a day.

As noted, the media provided in a presentation can take a variety of forms. In one example, a client is identified as having an anxiety symptom (e.g., anxiety based on mild dementia). To preempt an anxiety episode or in response to detection of a current or potential anxiety episode, a personalized presentation may be configured to play classical music and display nature and family photos from pleasant times to help calm the potential or current anxiety.

In another example, a client is identified as having a symptom of not drinking enough water. A personalized therapeutic presentation may be configured to periodically present an audio or audio/video message from a family member prompting the client to drink a glass of water. The familiar, trusted voice of a family member or friend is often more effective in prompting action over an unfamiliar, disembodied voice reminder or text prompting.

As a further example, a personalized therapeutic presentation may include more generic text or audio prompts to encourage other day-to-day behaviors, such as brushing teeth, attending meals, or going to bed.

In addition to the informant GUI 102, a data acquisition engine is responsive to a caregiver GUI 106. While an informant GUI 102 receives indication of symptoms and other data from ones having relationships with the client that may be familial or casual, the caregiver GUI 106 offers a mechanism for receiving further input from persons having a professional relationship with the client, when necessary. A caregiver GUI 106 provides a mechanism for approving symptoms identified for the client, setting or confirming treatment goals associated with approved symptoms, suggesting presentation assets to help achieve treatment goals, prioritizing symptoms, and providing other inputs. Inputs from the caregiver GUI 106 are stored in the treatment presentation data store 110. In some instances, such as for symptoms of low criticality, caregiver approval may not be required.

A treatment designer/adjuster GUI 108 provides an input for creating and adjusting personalized therapeutic presentations for the client. Presentations may be designed and adjusted automatically (e.g., continually based on a set of rules), based on designer/technician input, or semi-automatically based on a combination of automated generation and human input. In one example, certain symptoms are identified by an informant at 104 and approved by a caregiver at 106. An automated treatment designer module 108 may select certain presentation assets automatically based on the identified symptoms or goals (e.g., a text reminder asset may be scheduled to appear once every six hours that prompts a user to drink a glass of water). An automated design may further provide assets that are customized for the client. For example, when the treatment presentation data store 110 data indicates an anxiety symptom, the automated treatment designer 108 may schedule music to be played during periods of potential anxiety (e.g., at certain times, certain time intervals, or when other anxiety potential conditions are true). The data acquisition engine 102, in conjunction with the treatment presentation data store 110 and the treatment designer module 108 may be configured to identify music that is associated with the client (e.g., the client's favorite soothing music) to generate personalized presentations that have a higher degree of effectiveness.

Presentations can also be generated wholly by human identification of presentation assets or in a semi-automatic method where portions of the presentation are automatically generated and then adjusted by a caregiver or other technician via the treatment design GUI 108. For example, a presentation may be automatically generated based on identified symptoms or goals. The personalized therapeutic presentation is then adjusted by a caregiver having a relationship with the client to further personalize the presentation (e.g., include materials associated with client family members, client memories; adjust a presentation based on caregiver's experience with the client).

In addition to designing the personalized presentation using the GUI at 108, a therapeutic presentation can also be adjusted in an automated, manual, or semi-automatic fashion. Because at least portions of the presentation are aimed at achieving goals related to particular treatments, the effectiveness of the presentation can be evaluated based on whether the client is meeting the goals. When the client is progressing or meeting the goals, the treatment presentation may be kept the same or adjusted accordingly. When the client is not progressing or not progressing as quickly as hoped, the presentation can also be adjusted. For example, if a client continues to not drink enough water a day, more frequent prompts could be provided in the hopes that, while some promptings may be ignored, a certain portion of the prompts will be heeded, resulting in better achievement of the goal. As another example, stimuli in a presentation may be adjusted in the hopes of better achieving a goal. For example, where an initial presentation provided a text prompt to go to dinner on time is not resulting in the goal being met, the prompt may be changed to a video of a family member reminding the client that it is time to go to dinner.

Figure 2:
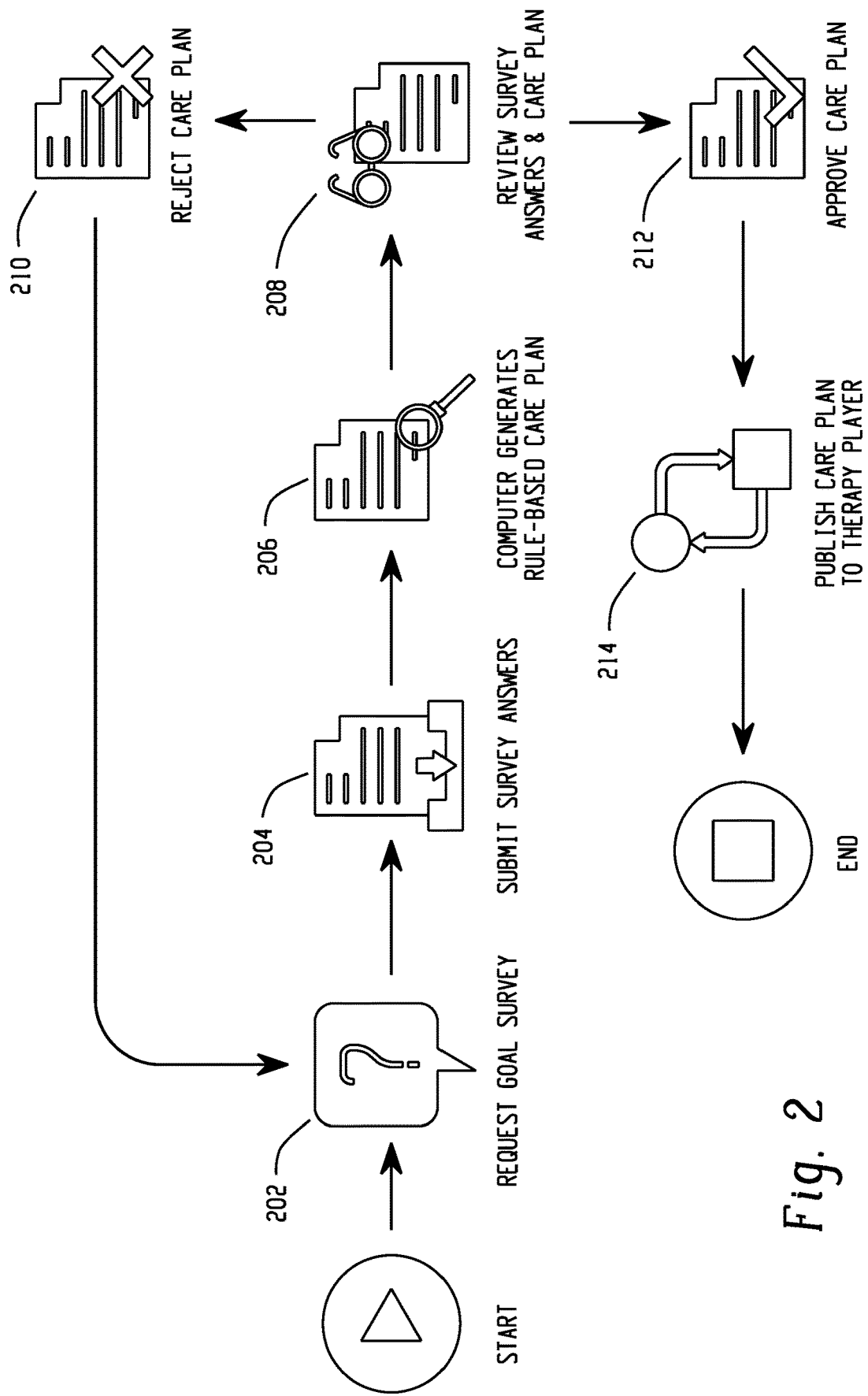
FIG. 2 is a flow diagram depicting an example process for generating a personalized therapeutic presentation.

FIG. 2 is a flow diagram depicting an example process for generating a personalized therapeutic presentation. A goal survey is requested at 202 by an informant, such as a family member, friend, or caregiver of a client, or the client themselves. The survey, which may be accessed via an informant GUI, is completed, with the informant providing information such as symptoms that they have observed for the client that they would like to have addressed. The survey is submitted at 204 and a rule based care plan is generated at 206 that includes an automated generation of a personalized therapeutic presentation. At 208, the computer-generated care plan is reviewed, such as by a caregiver or presentation design technician. During the review, the presentation may be wholly rejected as being inappropriate, as indicated at 210. When rejected, the presentation generation process can be restarted through a return to step 202. The presentation can also be wholly approved at 212 when the reviewer agrees that the presentation is in good form for the client. Further, the reviewer at 208 can adjust the presentation and then approve, making the presentation generation a semi-automatic process. The reviewer can adjust the presentation for appropriateness, based on knowledge interactions with the client or appropriate medical and psychological standards, or the reviewer can adjust the presentation to further personalize the presentation for the patient, adding family photos and favorite music, to make the presentation more attractive to the client.

After approval of the presentation at 212, the presentation is published to the therapy player used by the client. In one example, the therapy player is a tablet computer. A new or updated personalized therapeutic presentation is packaged and transmitted to the tablet computer, such as via a wireless link. The tablet computer is configured to play the presentation continuously or at scheduled times. In this manner, the personalized presentation can be continuously refined, without having to physically access the therapeutic player utilized by the client.

FIG. 3 depicts an example symptom survey that is provided to an informant via an informant GUI. A symptom survey allows an informant to flag issues that they see related to the client. Providing an opportunity for multiple parties to identify symptoms can greatly improve the effectiveness of a personalized care plan and presentation. A client may only exhibit certain symptoms with certain people or at certain times. Further, a client may be more willing to discuss certain symptoms with certain people (e.g., a client may be more willing to discuss certain symptoms with family than with a caregiver). The symptom survey facilitates identification of symptoms that requires little knowledge of medicine or client care techniques. An informant can simply identify an issue and know that the symptom will be addressed. Example symptoms that can be identified include behavioral symptoms such as delusions, anxiety, and confusion; sleep symptoms; social symptoms; and daily living/hygiene symptoms. Information from the symptom survey is received and stored in a treatment presentation data store.

FIG. 4 depicts an example goal form that is provided to a caregiver via a caregiver GUI. The goal form is populated with symptoms identified for a client, such as symptoms associated with the client in the treatment presentation data store via identification on a symptom survey received from a family member or friend of the client. The goal form enables a caregiver to provide feedback on symptoms identified for the client. The goal form can receive free text feedback from the caregiver or feedback via another mechanism such as a drop down menu that identifies whether an identified symptom is something that the caregiver agrees should be addressed along with reasons for that opinion. The caregiver can also identify potential goals that can be measured to determine progress on attempting to address the symptom in the free text field. If the identified symptom is a symptom that the caregiver does not think that the client should be treated for, the caregiver can identify such via a checkbox. The caregiver can further rank symptoms that are to be addressed via a priority ranking.

The goal form enables a level of professional feedback and control in the generation of a care plan and personalized presentation for a client. While informants, such as family members and friends, may identify symptoms with little medical and psychological knowledge, a caregiver can utilize a goal form to filter the set of symptoms for which a client is to be treated. Symptoms may not be treated for a variety of reasons, such as low priority symptoms (i.e., the patient could be overwhelmed if being treated for too many symptoms simultaneously) or symptoms for which the caregiver does see sufficient evidence.

A caregiver's feedback on a goal form is provided to a data acquisition engine for population of the treatment presentation data store. A personalized therapeutic presentation can be generated based on data provided via the goal form (and other sources, such as data from an informant). For example, presentation assets for symptoms that a caregiver does not agree are present may not be incorporated into the personalized presentation. Further, presentation assets associated with high priority symptoms may be incorporated into the personalized presentation with a higher frequency or using higher visibility assets (e.g., sound or video over simple text reminders).

FIG. 5 depicts an example goal definition form that is provided to a caregiver or other party via a caregiver GUI. In one example, the form depicted in FIG. 5 can be provided to other parties such as an informant. Having identified a set of symptoms to be treated, a goal definition form receives data that formally defines goals for a care plan and personalized presentation. The goal definition form includes a column for defining goals for each of the symptoms selected for treatment. In step 1, the goal definition form identifies the symptom and a general goal for the symptom (e.g., hydration, increase hydration; medication, increase compliance; agitation; reduce). Step two identifies the current status for that symptom. The current status should be described using a metric that can be observed and tracked (e.g., 0 glasses of water per day; 25% medication compliance; agitated 5 times per day). Step two further identifies an expected level for the symptom that serves as an overall goal for treatment of the symptom (e.g., 5 glasses of water per day; 90% medication compliance; agitated only 3 times per week). Step three identifies levels of the metric that indicate better than expected progress or less than expected progress (e.g., 7 glasses of water per day is identified as much more than expected, 6 glasses of water per day is identified as somewhat more than expected, 4 glasses of water per day is identified as somewhat less than expected, and 2 glasses of water per day is identified as much less than expected).

The metric levels that define current status may be prepopulated to help the caregiver formulate a correct and useful answer, and to create consistency across clients. For instance, if hydration is the concern, the goal definition form will ask to define the number of glasses the client drinks today. Other common metrics are percentages and hours or minutes (e.g., number of hours agitated per day).

The metric levels that define desired ('optimal') status, suboptimal status and supra-optimal status may be provided using an algorithm in combination with lower and upper bounds depending on the symptom at hand. For instance, if hydration is of concern, the desired status is set automatically XX percent higher than the current status and is not to exceed Y glasses per day. The supra and suboptimal levels are derived accordingly using the algorithm.

The caregiver or informant approves the metrics if they meet their goals and expectations, or request an adjustment.

The metric levels entered into the goal identification form provide concrete standards by which a care plan and personalized therapeutic presentation can be evaluated. When a client reaches or is progressing toward a goal, a presentation can be maintained in a current state, or can be adjusted (e.g., to include encouragement and congratulations for progress). When presentation is not resulting in a client progressing, the presentation can be reevaluated and adjusted to attempt to improve results. Data from the goal identification form is provided to the treatment presentation data store and is utilized in evaluating and adjusting personalized presentations automatically or with the aid of technician or caregiver input.

Progress towards goals is assessed at regular intervals or when requested or necessary using subjective and objective metrics. The caregiver or informant may be reminded of the goals and be requested to provide subjective and objective feedback regarding the client's current status for each and every goal.

FIG. 6 is a presentation asset identification form utilized in the design of a personalized therapeutic presentation. The asset identification form identifies the types of assets that should be incorporated into a personalized presentation to meet particular goals. For each goal, one or more assets are identified related to topics to be displayed, pictures to be included, music to be played, trusted voices to be included, captions to be displayed, and a schedule for display that includes particular times or frequencies for displaying assets related to that goal (e.g., high priority goals can have presentation assets displayed more frequently). Data indicated on the asset identification form can be generated by a human, such as a caregiver or presentation design technician, or the data can be automatically generated by a computer based on a system of presentation generation rules, where the automatically generated presentation can access and include personalized content in the treatment presentation data store that is associated with the client for whom the presentation is being generated. Data indicated on the asset identification form is stored in the treatment presentation data store for use in designing a personalized presentation that is to be provided to the client.

Figure 7:
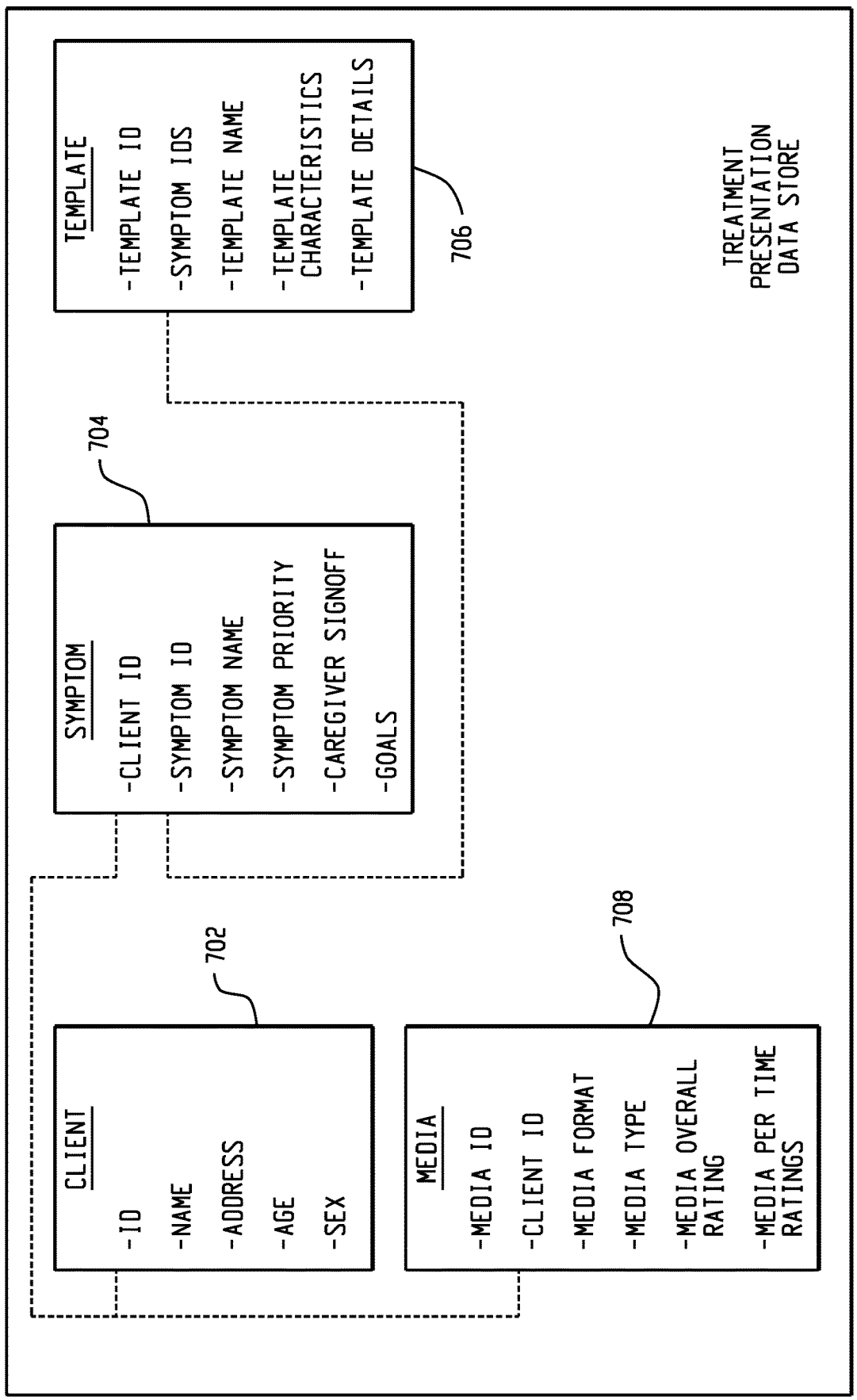
FIG. 7 is a diagram depicting an example schema for storing data in a treatment presentation data store.

FIG. 7 is a diagram depicting an example schema for storing data in a treatment presentation data store. A client record 702 includes identification data related to a client. The table includes a client identification number, a client name, address, age, and sex. The treatment presentation data store further includes one or more symptom records 704 associated with the client record via the client identification field. The symptom record identifies a symptom identified for the client (e.g., via a symptom survey) by a symptom identification number. The symptom record may further include a name of the symptom, a priority assigned to the symptom for that client, an identification of a caregiver who signed off on treatment of the symptom for the client, and goals defined for measuring progress of the client on treatment of the symptom.

The treatment data store may further include presentation template records 706. For example, the data store may include a presentation template record 706 that is associated with a particular symptom via a symptom identifier. The template record 706 identifies a base set of one or more presentation assets that are to be incorporated into a personalized therapeutic presentation to treat the identified symptom. For example, for a symptom of poor medication compliance, the template may indicate that a text reminder presentation asset should be included in a personalized presentation along with a trusted voice reminder from a person associated with the client. The fields of the template record 706 can include a template identification, a template name, characteristics of the template, and details of the template that include an identification of presentation assets that are to be included in a base treatment of the indicated symptom.

A template can be used to populate a presentation for a client based on symptoms and goals identified for the client. A base presentation, as prescribed by one or more templates, may be utilized for a client, or a base presentation can be augmented by a caregiver, presentation design technician, or other personnel in an attempt to further improve the personalized presentation.

The treatment presentation data store may further include media records 708. Media records 708 indicate certain presentation assets that can be incorporated into a personalized presentation. Some media is associated with individual clients. For example, a media record 708 could identify an audio recording of loved one of a particular client reminding that client to take their medication. Other media may be generic and unassociated with any particular client. For example, a picture of flowers in the sun may be a media presentation asset that can be assigned to any client, for example for treatment of a depression symptom. Media record fields can include a media identifier, a client identifier, a media format, a media type, a media overall rating (e.g., a field that identifies the effectiveness of that media in treating certain symptoms), and a media per time rating (e.g., an effectiveness per time length of media metric).

Figure 8:
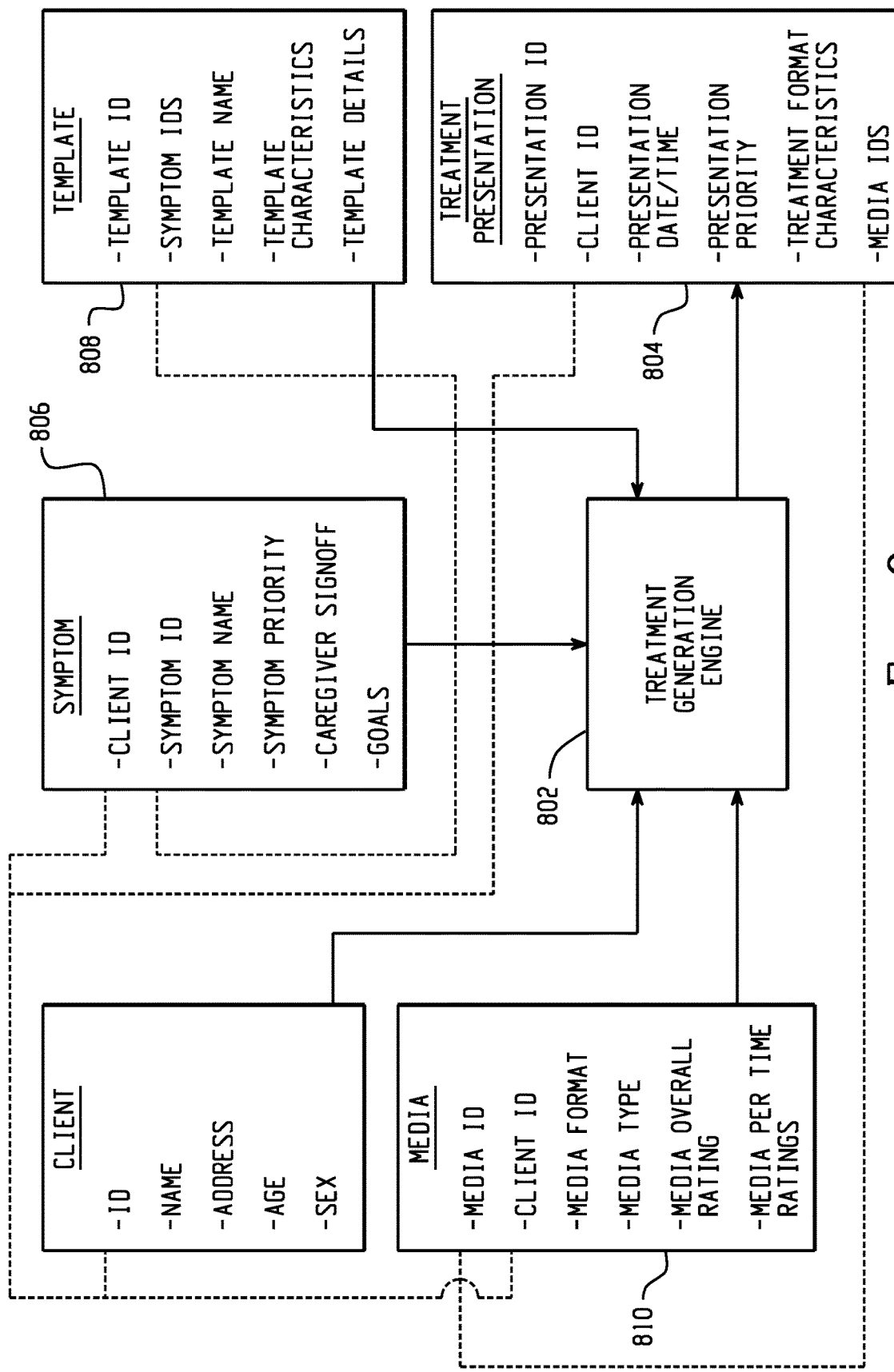
FIG. 8 is a diagram depicting the utilization of fields in a treatment presentation data store in generating a personalized treatment presentation for a client.

FIG. 8 is a diagram depicting the utilization of fields in a treatment presentation data store in generating a personalized treatment presentation for a client. A treatment generation engine 802 accesses records from the data store in order to generate one or more treatment presentation records for the client. A treatment presentation record 804 includes a presentation identifier and a client identifier that indicates the client with which the treatment presentation is associated. The presentation record further includes a presentation date and time that is populated if the treatment presentation is scheduled to be shown at a particular date/time or time of day (e.g., a brush teeth presentation may be scheduled for display daily at 8:30 PM). Some presentations can be shown at particular times, while other presentations can be shown periodically, such as based on a priority associated with the presentation (e.g., presentations can be continually run in a client's room from 8:00 AM-9:00 PM, where presentations associated with high priority symptoms can be displayed more frequently).

Details of the treatment presentation, such as the runtime length of the treatment presentation can be identified in the treatment presentation record 804. Further, the treatment presentation record 804 indicates presentation assets that are included in the personalized therapeutic presentation associated with the record 804 including indications of media to be included via media identifiers. For example, a treatment presentation record 804 associated with an anxiety symptom for a user may have a high priority, and thus be scheduled to run frequently throughout the day. The anxiety treatment presentation record may indicate the length of the anxiety presentation (e.g., 2 minutes, 30 seconds), and presentation assets included in the presentation, and in some cases, further, their order (e.g., the presentation is to display family pictures for 1:30 with soothing music, followed by pictures from a vacation that the client took with friends for 0:45, followed by a 0:15 voice recording from a family member). Such a presentation can help calm a client, such as a client that has exhibited signs of dementia, by reminding the client that they are in a safe place where they are happy, reducing anxiety.

A treatment presentation record 804 can be populated automatically through the use of rules and template. When a symptom record 806 for a client is approved, a treatment presentation record 804 may be generated for the client. A template record 808 associated with the symptom is accessed, where the template record 808 identifies presentation assets that are included in a base presentation for treatment of the symptom. For example, the template may indicate that family pictures should be displayed for 1:30 with soothing music, followed by life event pictures for 0:45, followed by a trusted voice for 0:15. While the template's indication of presentation assets is generic, the treatment generation engine 802 can access media records 810 (e.g., accessing family pictures, pictures from an client event, such as a trip, and a trusted voice of a family member speaking) associated with the particular client, so that the generated treatment presentation is customized and better suited for treatment of the particular client.

Figure 9:
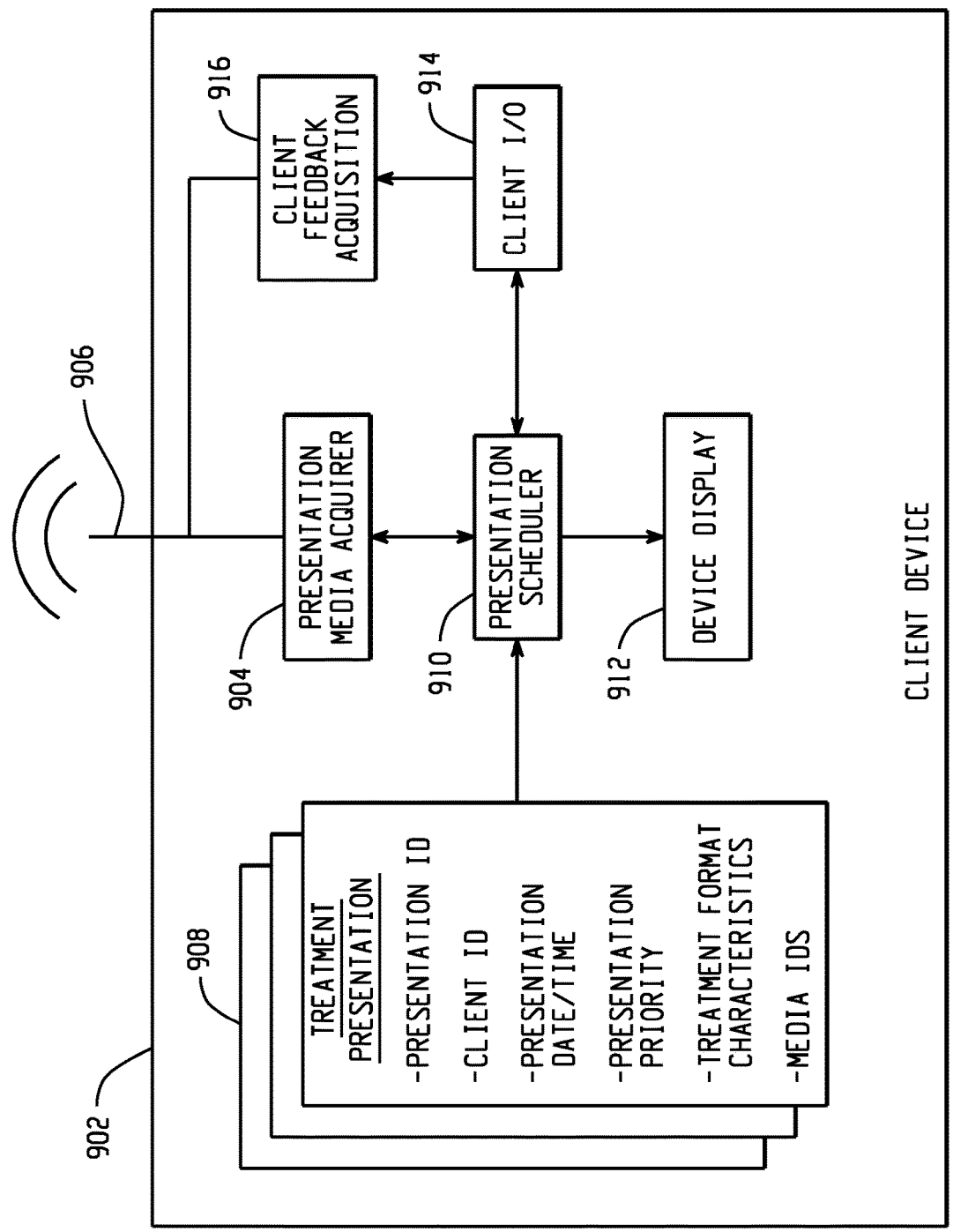
FIG. 9 is a block diagram of a client device, such as a tablet computer, for providing a personalized therapeutic presentation to a client.

FIG. 9 is a block diagram of a client device, such as a tablet computer, for providing a personalized therapeutic presentation to a client. The client device 902 includes a presentation media acquirer 904 that is responsive to a wireless transmitter/receiver 906. The presentation media acquirer 904 accesses personalized therapeutic presentation data associated with presentations to be presented to a client, such as from a server that includes a treatment generation engine. For example, the media acquirer 904 can acquirer one or more treatment presentation records 908 along with media associated with the presentation records 908 for storage on the client device 902. Media identified by the treatment presentation records 908 may be pre-accessed and stored at the client device 902, or such media may be accessed as needed for a presentation (e.g., streaming video). A presentation scheduler 910 accesses the treatment presentation records 908 to display personalized therapeutic presentations via a display device 912 of the client device 902. Presentations may be displayed according to a schedule or priority indicated by treatment presentation records 908. For example, presentations may be made continuously throughout a day or periods of a day or during a time period where the client is accessing the client device 902, with higher priority presentations appearing more frequently than low priority presentations.

The client device 902 may also be configured to receive user input via a user I/O device 914. In the example where the client device 902 is a tablet device, the client I/O device 914 is a touch screen device. Client input can be utilized for identifying treatment presentations 908 that should be displayed for the client as well as for gathering client feedback regarding the effectiveness of personalized presentations. In the first instance, a client device 902 may be configured to prompt a client about their current feelings. If the client indicates feelings of anxiousness via the client I/O, the presentation scheduler 910 can access a treatment presentation record 908 associated with anxiety reduction and provide that personalized presentation via the device display 912. A presentation scheduler 910 can further schedule presentations for display based on other inputs, such as the weather (e.g., display an anti-depression presentation in the case of gloomy weather), the news (e.g., display an anti-anxiety presentation during times of troubling news), or other events (e.g., a birthday presentation), provided to the client device 902, such as via the wireless receiver 906.

Feedback from the client can also be acquired at 916 for transmission back to a server having a treatment generation engine or treatment evaluation engine. Treatment presentation records can be newly created or augmented to adjust presentations based on the client feedback (e.g., if the client indicates a new symptom; if the client indicates that a currently displayed presentation is not effective). New or revised presentations can be communicated wirelessly back to the client device 902 based on the client feedback in an attempt to provide more effective therapeutic presentations.

Figure 10:
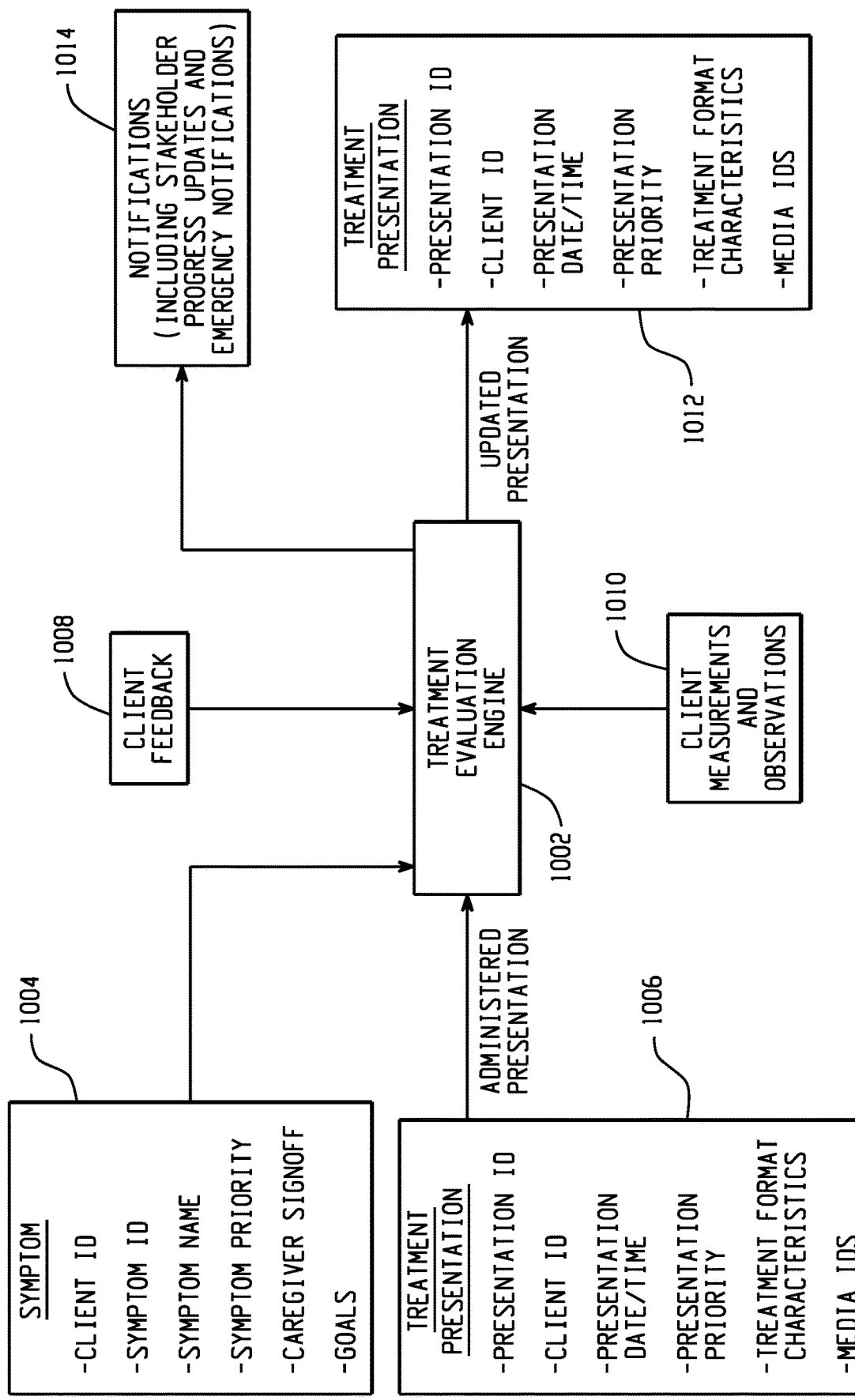
FIG. 10 is a diagram depicting example inputs and outputs of a treatment evaluation engine.

FIG. 10 is a diagram depicting example inputs and outputs of a treatment evaluation engine. Because of the highly variable nature of clients, presentation assets that work well for one client may not work well for another client. A treatment evaluation engine 1002 is configured to adjust and rework existing personalized therapeutic presentations to attempt to achieve improved results. A treatment evaluation engine 1002 receives an indication of a symptom being treated, such as via a symptom record 1004 and details of a presentation that was provided to a client via a treatment presentation record 1006. Feedback on the effectiveness of the administered presentation 1006 can be received from multiple sources. For example, feedback can be received from the client 1008, such as feedback entered via an I/O device associated with the mechanism used to display the presentation to the client. Further feedback 1010 can be received via measurements from parties observing the client, such as family members or caregivers. That feedback can be in the form of concrete data observations, such as data related to established goals for a symptom treatment (e.g., the client drank 6 glasses of water today; the client had 2 anxiety episodes today). The feedback can also be more qualitative, such as a family member indicating that a presentation upset the client or otherwise was ineffective.

Based on the received data, the treatment evaluation engine 1002 can generate an updated presentation record 1012 that attempts to improve the efficacy of the administered treatment presentation 1006. The changes to the updated presentation 1012 may be minor or major depending on the feedback 1008, 1010 received. Minor feedback may include a slight change in visual elements displayed (e.g., a picture of a stream instead of a sunflower in an anti-anxiety presentation), while major feedback may include a total rework of a presentation (e.g., removal of all audio media from a presentation for a client who is having severe headaches).

The treatment evaluation engine 1002 can also serve a notification function, as indicated at 1014. The treatment evaluation engine 1002 can be configured to store and provide periodic reports on progress, such as progress as compared to symptom treatment goals, to caregivers, such as doctors or social workers. The treatment evaluation engine 1002 can also provide alerts, such as emergency notifications, when deemed appropriate (e.g., when feedback indicates sudden cognitive decline, such as a client providing gibberish I/O feedback, that could indicate onset of a serious physical ailment such as a stroke; when a client provides I/O feedback that indicates suicidal thoughts).

Figure 11:
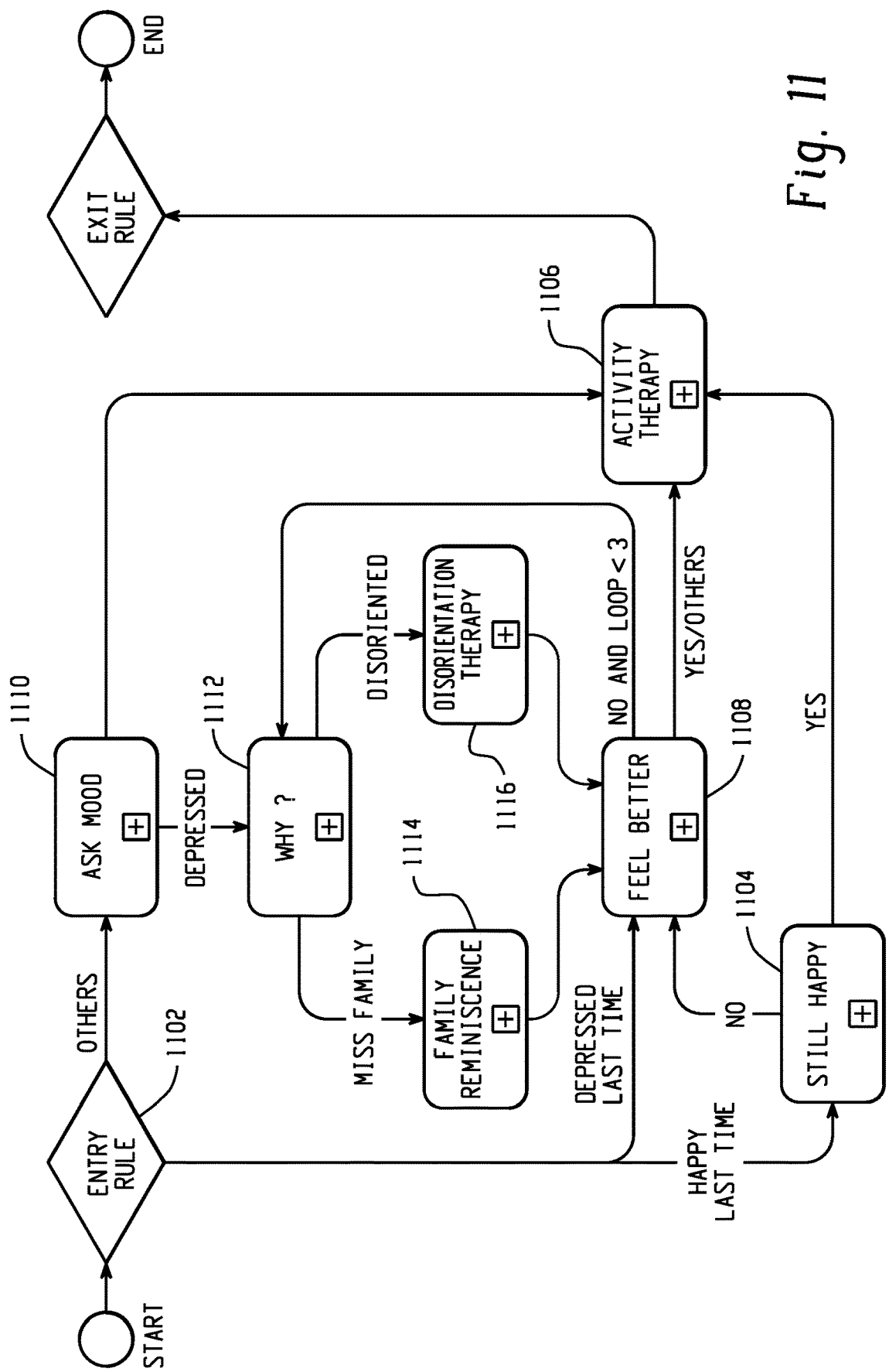
FIG. 11 is an example set of rules and corresponding presentation assets for providing an interactive presentation to a client.

FIG. 11 is an example set of rules and corresponding presentation assets for providing an interactive presentation to a client. An interactive presentation begins at 1102 with analysis of an entry rule that inquires as to the client's mood during a last time the presentation was displayed. If the client previously indicated that they were happy, then a presentation asset is displayed that makes an inquiry 1104 as to whether the client is still happy. If the client is still happy, then the presentation proceeds to 1106 for activity therapy, as described in further detail with relation to FIG. 12. If the client previously indicated that they were depressed, then a presentation asset is displayed at 1108 asking whether the client is feeling better. If the client is feeling better, then the presentation proceeds to activity therapy at 1106. If the client identifies at 1108 or 1110 that they are feeling depressed, then a presentation asset is displayed at 1112 that inquires as to why the client is feeling depressed. If the client indicates that they miss their family, then a collection of presentation assets are displayed at 1114 that provides family reminders, such as pictures and audio/video recordings. If the client indicates that they are disoriented, then a disorientation therapy presentation is displayed at 1116.

Presentation assets may consist of single presentation displays. Presentation assets may also comprise collections of other presentation assets, as indicated by the activity therapy asset 1106, the family reminiscence presentation asset 1114, and the disorientation therapy presentation asset 1116. Such group presentation assets facilitate incorporation of blocks of presentation assets into presentation programs without the need for manipulation of every individual presentation asset.

Figure 12:
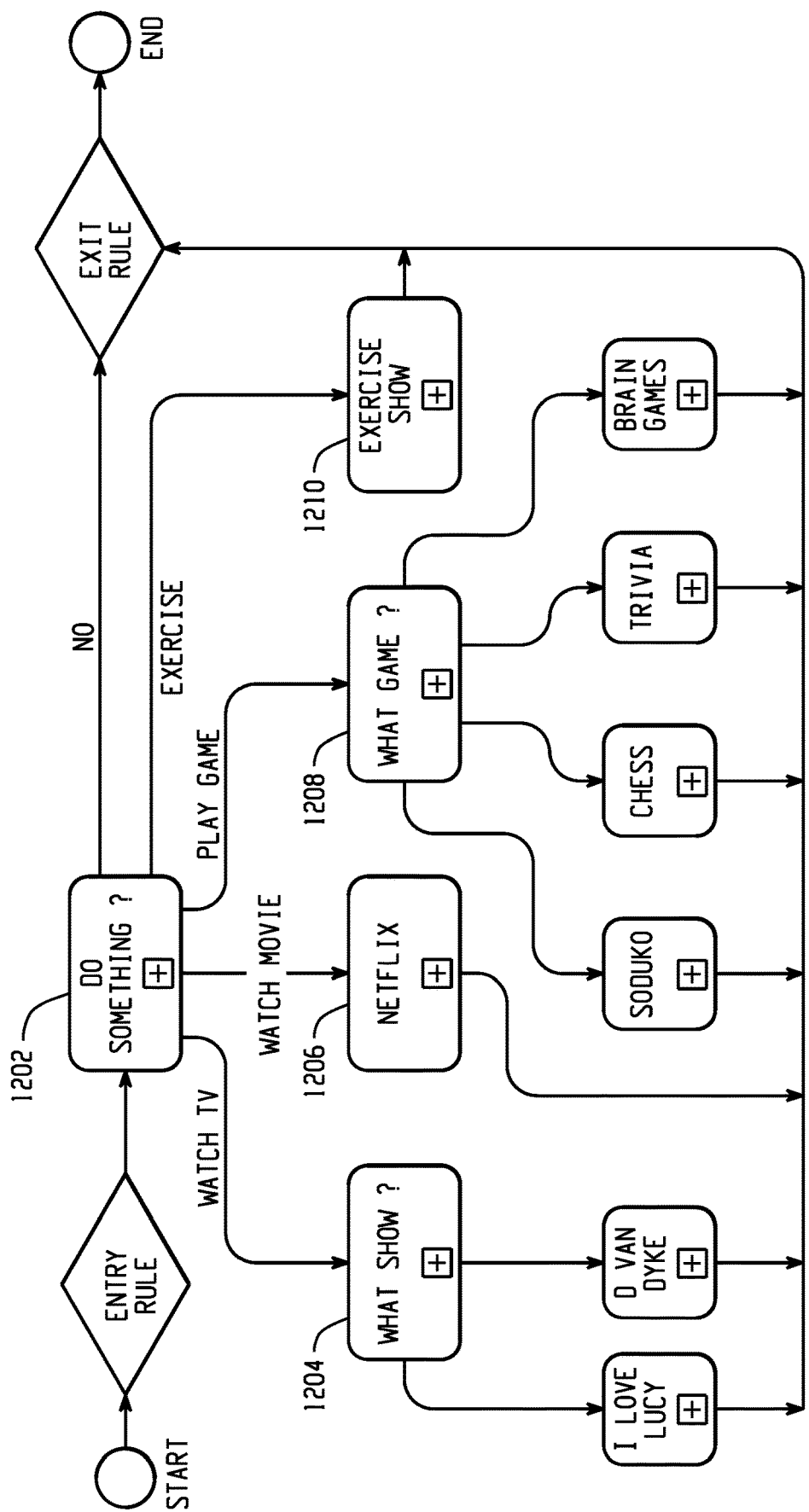
FIG. 12 is a diagram depicting example presentation assets contained within the activity therapy presentation asset.

FIG. 12 is a diagram depicting example presentation assets contained within the activity therapy presentation asset. At 1202, a client is asked whether they would like to perform an activity using the client device. If a client indicates a desire to watch television, then a presentation asset is provided that inquires as to which show the client would like to watch at 1204, and the client can then be provided that show via the client device or other device. If a client indicates a desire to watch a movie, then a presentation asset that is configured to solicit a movie selection is displayed at 1206. If a client indicates a desire to play a game, then a presentation asset that includes a menu of games is displayed at 1208, with a game being provided to the client upon selection. If the client indicates a desire to exercise, then a presentation asset is displayed at 1210 in the form of an exercise video, such as on the client device.

Figure 13:
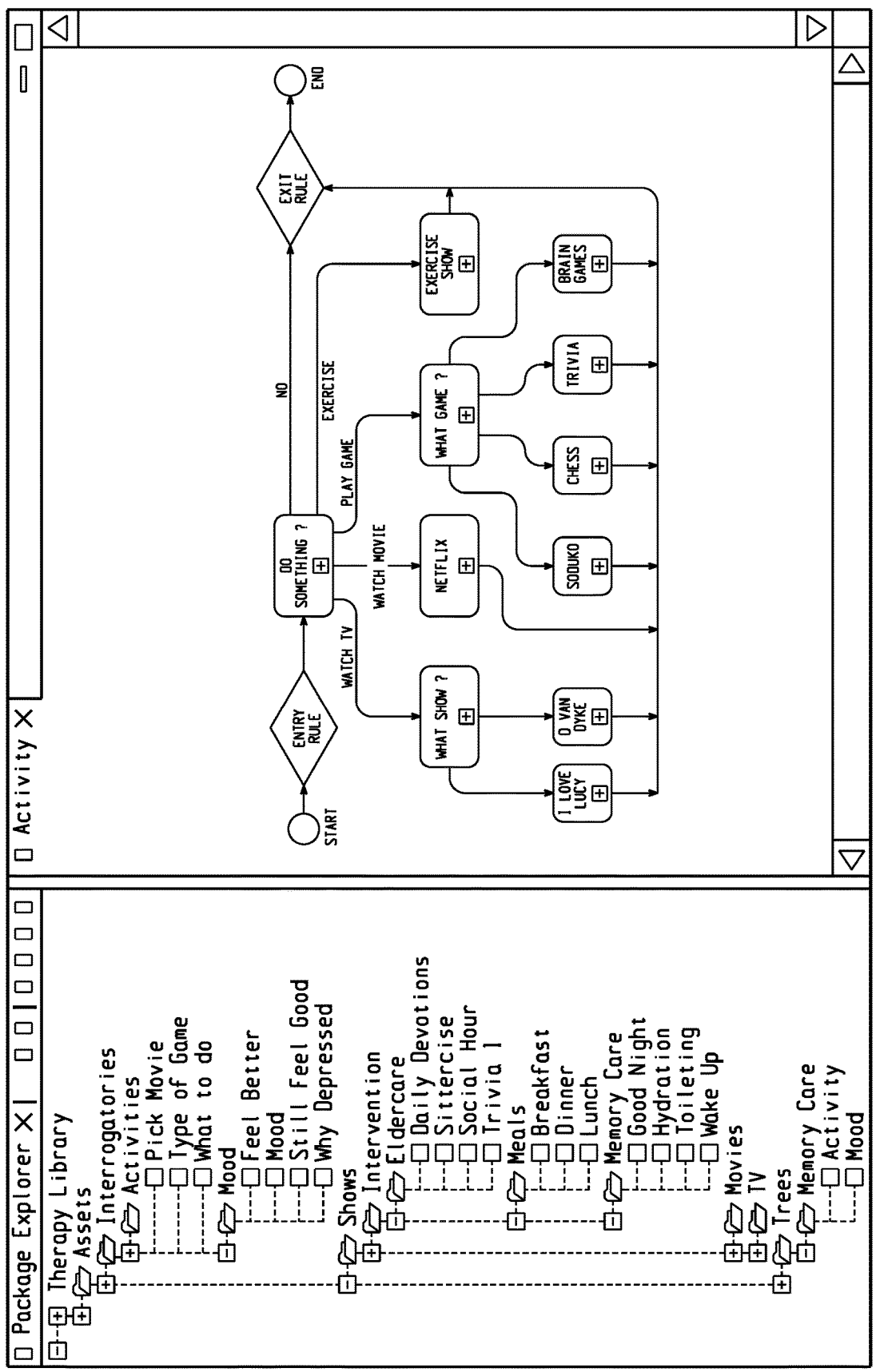
FIG. 13 displays an example interface for manipulating a therapeutic presentation.

As indicated previously, presentations can be generated automatically, manually, or semi-automatically. FIG. 13 displays an example interface for manipulating a therapeutic presentation. An initial version of the depicted presentation could be automatically generated through the use of templates. The initial version could also be manually generated by a caregiver or presentation design technician. Regardless of the origination of the presentation, the GUI of FIG. 13 facilitates editing of presentations. A left-hand window contains a collection of presentation assets that can include individual and groups of presentation assets that can be included in a presentation. The presentation assets can be dragged or otherwise inserted into the right window. There, flows and rules for progressing among the presentation assets during a presentation can be defined. The presentation can then be saved in a treatment presentation data store, such as in a treatment presentation record, where that treatment presentation record can be transmitted to a client for display.

This application uses examples to illustrate the invention. The patentable scope of the invention includes other examples.

It is claimed:

1. A computer-implemented system for providing a personalized therapeutic presentation, comprising:
　　a treatment presentation data store configured to store one or more data structures associated with a personalized therapeutic presentation for a client in connection with a therapeutic treatment of a symptom of the client, wherein the one or more data structures include client data and template data, wherein the client data comprises scheduling information for at least one activity associated with the client, wherein the template data comprises a plurality of dynamic template records respectively associated with each of a plurality of activities, wherein each dynamic template record of the plurality of dynamic template records identifies a plurality of media elements and a configuration in which the media elements of the plurality of media elements are to be presented to the client, wherein the configuration of media elements represents the scheduling information for the at least one activity;
　　a treatment generation engine configured to generate a treatment presentation for the client based on data stored in the treatment presentation data store, wherein the treatment presentation is designed to alert the client of the at least one activity identified by the client data, wherein the treatment presentation comprises a presentation of media elements configured according to a particular dynamic template record associated with the at least one activity; and
　　a treatment presentation evaluation engine, wherein the treatment presentation evaluation engine is configured to update the treatment presentation based on weather information or news information to generate an updated treatment presentation, wherein updating the treatment presentation comprises changing at least one of the media elements of the treatment presentation, wherein the updated treatment presentation is transmitted to a client device for display of the updated treatment presentation.

2. The system of claim 1, wherein the updated treatment presentation is configured to receive interactive input from the client during presentation of the media elements, and wherein the updated treatment presentation is configured to adapt the presentation of media elements based on the interactive input received from the client.

3. The system of claim 2, wherein the treatment presentation evaluation engine is configured to adjust the updated treatment presentation after the treatment presentation has been presented based on the interactive input received from the client.

4. The system of claim 1, wherein the updated treatment presentation is stored in the treatment presentation data store in a treatment presentation data record, wherein presentation data from the treatment presentation data record is transmitted to the client device for display of the updated treatment presentation.

5. The system of claim 4, wherein the treatment presentation is an audio presentation, a video presentation, or an audio/video presentation.

6. The system of claim 5, wherein the client device is a desktop computer, a laptop computer, a tablet computer, a mobile phone, a smart phone, or a television.

7. The system of claim 4, wherein the treatment presentation data record identifies schedule data associated with the treatment presentation, wherein the schedule data includes a presentation frequency, a presentation day, a presentation date, or a presentation time.

8. The system of claim 1, wherein the treatment presentation data store stores client symptom data for multiple symptoms associated with the client and a priority ranking of the multiple symptoms.

9. The system of claim 8, wherein the treatment generation engine generates the treatment presentation based on the priority ranking.

10. The system of claim 9, wherein a symptom having a high priority ranking has more media elements associated with that symptom incorporated into the treatment presentation, or a treatment presentation associated with the high priority ranking is scheduled to be presented more frequently than lower priority ranked symptoms.

11. The system of claim 1, wherein each dynamic template record
further identifies a duration of each media element.

12. The system of claim 1, wherein the treatment generation engine selects personalized media for the treatment presentation based on the dynamic template record and an association between particular media elements and the client.

13. The system of claim 1, wherein the treatment presentation evaluation engine is configured to update the treatment presentation after the treatment presentation has been presented to the client.

14. The system of claim 13, wherein the treatment presentation evaluation engine updates the treatment presentation based on client goal data and a client observation.

15. The system of claim 14, wherein the treatment presentation is updated based upon a comparison of the client observation to the client goal data.

16. The system of claim 15, wherein the treatment presentation is updated multiple times based upon continued comparisons of client observations to the client goal data.

17. The system of claim 13, wherein the treatment presentation is updated based upon a client feedback.

18. The system of claim 1, wherein the client device comprises a tablet device, wherein the tablet device accesses the media elements for the treatment presentation wirelessly.

19. The system of claim 1, further comprising a data acquisition engine, wherein the data acquisition engine is configured to provide one or more graphical user interfaces to a client caregiver, a client informant, or a treatment designer/adjuster to capture data for storage in the treatment presentation data store.

20. The system of claim 19, wherein a first graphical user interface receives client symptom data from a client informant who is familiar with the client, and wherein a second graphical user interface receives a confirmation and symptom priority ranking from a caregiver associated with the client.

21. The system of claim 19, wherein the data acquisition engine captures data from multiple ones of the client caregiver, the client informant, and the treatment designer/adjuster, wherein the system further comprises:
a presentation rules data store containing rules for automatically generating treatment presentations, wherein the treatment generation engine generates the treatment presentation further based on the rules and data acquired by the data acquisition engine.

22. The system of claim 1, further comprising a reporting engine, wherein the reporting engine is configured to transmit a status update message to a stakeholder based on a comparison of client goal data and a client observation.

23. The system of claim 22, wherein the stakeholder is a family member or a care giver of the client.

24. The system of claim 22, wherein the reporting engine is configured to identify an emergency situation based upon the client observation, wherein the reporting engine is configured to contact a first responder based on the identification of the emergency situation.

25. The system of claim 24, wherein the emergency situation is identified based upon a client response to a question presented to the client during the treatment presentation.

26. A computer-implemented method of providing a personalized therapeutic presentation, comprising:
accessing a treatment presentation data store in response to a signal to generate a personalized therapeutic presentation for a client, the treatment presentation data store storing one or more data structures associated with the personalized therapeutic presentation for a client in connection with a therapeutic treatment of a symptom of the client, the one or more data structures comprising client data and template data, the client data comprising scheduling information for at least one activity associated with the client, the template data comprising a plurality of dynamic template records respectively associated with each of a plurality of activities, each dynamic template record of the plurality of dynamic template records identifying a plurality of media elements and a configuration in which the media elements of the plurality of media elements are to be presented to the client, the configuration of media elements representing the scheduling information for the at least one activity;
generating a treatment presentation for the client based on data stored in the treatment presentation data store, wherein the treatment presentation is designed to alert the client of the at least one activity identified by the client data, wherein the treatment presentation comprises a presentation of media elements configured according to a particular dynamic template record associated with the at least one activity; and
updating the treatment presentation based on weather information or news information to generate an updated treatment presentation, wherein updating the treatment presentation comprises changing at least one of the media elements of the treatment presentation, wherein the updated treatment presentation is transmitted to a client device for display of the updated treatment presentation.

* * * * *

UNITED STATES PATENT AND TRADEMARK OFFICE
CERTIFICATE OF CORRECTION

PATENT NO. : 12,243,632 B2
APPLICATION NO. : 17/985219
DATED : March 4, 2025
INVENTOR(S) : Chantal Kerssens et al.

Page 1 of 1

It is certified that error appears in the above-identified patent and that said Letters Patent is hereby corrected as shown below:

In the Claims

Column 14, Line 15, Claim 23, delete "care giver" and insert -- caregiver --

Signed and Sealed this
Twenty-seventh Day of May, 2025

Coke Morgan Stewart
*Acting Director of the United States Patent and Trademark Office*